United States Patent [19]

VandenBerg

[11] Patent Number: Plant 7,754

[45] Date of Patent: Dec. 24, 1991

[54] CHRYSANTHEMUM PLANT NAMED EMILY

[75] Inventor: Cornelis P. VandenBerg, Salinas, Calif.

[73] Assignee: Yoder Brothers, Inc., Barberton, Ohio

[21] Appl. No.: 565,708

[22] Filed: Aug. 13, 1990

[51] Int. Cl.[5] ..... A01H 5/00

[52] U.S. Cl. ..... Plt./76

[58] Field of Search ..... Plt./76, 80, 81, 74, Plt./82.4, 74.1

*Primary Examiner*—Howard J. Locker

*Attorney, Agent, or Firm*—Foley & Lardner

[57] ABSTRACT

A Chrysanthemum plant named Emily particularly characterized by its flat capitulum form; decorative capitulum type with many disc florets; light pink ray floret color, with darker center of the flower; diameter across face of capitulum of 57 to 70 mm when fully opened; spreading and prolific branching pattern, with 8 to 9 breaks after pinch when grown outside under natural daylength in fall flowerings, and 6 to 7 breaks after pinch when grown in 10 cm pots for spring flowerings; natural season flowering date of August 20 to 25 when planting rooted cuttings June 21 to 23 in Salinas, Calif., and September 27 to 29 when planting rooted cuttings June 15 to June 18 in Hightstown, N.J.; flowering response of 47 to 48 days after rooting in no light/no shade programs in spring; plant height of 36 cm when grown in fall under natural daylength with no growth regulators in New Jersey, of 23 to 25 cm when grown in fall under natural daylength with no growth regulators in California, and of 23 to 25 cm when grown in 10 cm pots in spring with 1 to 2 applications of 2500 ppm B-9 SP; and durable, uniform performance.

3 Drawing Sheets

The present invention comprises a new and distinct cultivar of Chrysanthemum, botanically known as *Dendranthema grandiflora*, and referred to by the cultivar name Emily.

Emily, identified as 87-284001, was originated from an open pollination program, where the best breeding lines were selected by Cornelis P. VandenBerg, flowered under controlled conditions outdoors and left to be pollinated by bees, in Salinas, Calif., in 1986.

The female parent of Emily was an unnamed seedling, identified as 85-013002, and described as a pink decorative garden mum having many disc florets, a natural season flowering date of August 29 to September 3 in Salinas, Calif., and of October 1 to 8 in Hightstown, N.J., a flowering response in spring of 53 to 58 days, a plant height of 33 to 36 cm in fall natural season flowerings in New Jersey, a height of 18 to 23 cm in fall natural season flowerings in California, and a height of 18 cm in spring flowerings in 10 cm pots with no growth regulator. Information as to the capitulum diameter of the female parent is not currently available. The female parent was discarded from the breeding program in October 1988.

The male parent of Emily is unknown, since the female parent of Emily was open pollinated.

Emily was discovered and selected as one flowering plant within the progeny of the stated cross by Cornelis P. VandenBerg in October of 1987, in a controlled environment in Salinas, Calif.

The first act of asexual reproduction of Emily was accomplished when vegetative cuttings were taken from the initial selection in December 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Emily are firmly fixed and are retained through successive generations of asexual reproduction.

Emily has not been observed under all possible environmental conditions. The phenotype may vary significantly with variations in environment such as temperature, light intensity and daylength.

The following observations, measurements and comparisons describe plants grown in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Emily, which, in combination, distinguish the Chrysanthemum as a new and distinct cultivar:

1. Flat capitulum form.
2. Decorative capitulum type with many disc florets.
3. Light pink ray floret color, with the center of the flower being a darker pink.
4. Diameter across face of capitulum of 57 to 70 mm. when fully opened.
5. Branching pattern is spreading and prolific, with 8 to 9 breaks after pinch when grown outside under natural daylength in fall flowerings, and 6 to 7 breaks after pinch when grown in 10 cm pots for spring flowerings.
6. Natural season flower date of August 20 to 25 when planting rooted cuttings on June 21 to June 23 in Salinas, Calif., and of September 27 to 29 when planting rooted cuttings June 15 to June 18 in Hightstown, N.J.
7. Flowering response of 47 to 48 days after rooting in no light/no shade programs in spring.
8. Plant height of 36 cm when grown in fall under natural daylength with no growth regulators in New Jersey, of 23 to 25 cm when grown in fall under natural daylength in California, and of 23 to 25 cm when grown in 10 cm pots in spring with 1 to 2 applications of 2500 ppm B-9 SP.

9. Durable, uniform performance.

The accompanying photographic drawings show typical inflorescence and leaf characteristics of Emily, with the colors being as nearly true as possible with illustration of this type.

Sheet 1 is a color photograph of Emily grown as a pinched spray pot mum with 4 cuttings in a 15 cm. pot.

Sheet 2 is a black and white photograph of three views of the inflorescence of Emily.

Sheet 3 is a black and white photograph showing the upper and under sides of the leaves of Emily at 3 stages of development (mature, intermediate and immature).

Sheets 2 and 3 include a measuring tape in centimeters, thereby illustrating the flower and leave dimensions.

No commercial cultivar known to the inventor is closely comparable to Emily. The very light pink ray floret color with the darker center of the flower, together with the high number of disc florets, is not represented in commercial cultivars known to the inventor. The most similar in comparison to Emily might be the commercial cultivar Debonair, disclosed in U.S. Plant Pat. No. 5,324. Reference is made to attached Chart A, which compares certain characteristics of Emily to the same characteristics of Debonair.

Similar traits are capitulum form and type, with Emily having more disc florets than Debonair. Natural season flower date in New Jersey is comparable. Emily has a lighter ray floret color, more breaks after pinch, an eariler natural season flowering response in Salinas, Calif. and an earlier flowering response in spring when compared with Debonair. Since filing the application resulting in the plant patent for Debonair, more detailed information from different locations has been collected for Debonair, which information is presented in Chart A.

In comparison to the female parent, Emily has a significantly earlier flowering response in fall natural season flowerings and also in small pot spring flowerings.

In the following description color references are made to The Royal Horticultural Society Colour Chart. The color values were determined on plant material grown as a pinched spray pot mum in Salinas, Calif. on May 1, 1990.

Classification:

*Botanical.*—*Dendranthema grandiflora* cv Emily.

*Commercial.*—Flat decorative spray pot mum and garden mum.

INFLORESCENCE

A. Capitulum:

*Form.*—Flat.

*Type.*—Decorative, with many ray florets.

*Diameter across face.*—57 to 70 mm. when fully opened.

B. Corolla of ray florets:

*Color (general tonality from a distance of three meters).*—Light Pink with darker center of flower.

*Color.*—Upper surface: Center of flower closest to 80D, with outer petals 75B. Under surface: 75B.

*Shape.*—See photograph.

C. Corolla of disc florets:

*Color (mature).*—6B.

*Color (immature).*—2A, overlaid with 144B.

D. Reproductive organs:

*Androecium.*—Present on disc florets only; moderate pollen.

*Gynoecium.*—Present on both ray and disc florets.

PLANT

A. General appearance:

*Height.*—36 cm grown in fall under natural daylength with no growth regulators in New Jersey, 23 to 25 cm when grown in fall under natural daylength in California, and of 23 to 25 cm when grown in 10 cm pots in spring with 1 to 2 applications of 2500 ppm B-9 SP.

*Branching pattern.*—Spreading and prolific, with 8 to 9 breaks after pinch when grown outside under natural daylength in fall flowerings, and 6 and 7 breaks after pinch when grown in 10 cm pots for spring flowerings.

B. Foliage:

*Color (upper surface).*—147A.

*Color (under surface).*—147B.

*Shape.*—See photograph.

CHART A

| CULTIVAR | EMILY | DEBONAIR |
|---|---|---|
| Ray floret color | Light pink with darker center | Purple |
| Capitulum form and type | Flat decorative with many disc florets | Flat decorative |
| Diameter across face of capitulum | 57 to 70 mm | 57 to 64 mm |
| Branching pattern | Spreading and prolific | Spreading |
| Breaks-fall outdoors | 8 to 9 | 6 to 7 |
| Breaks in 10 cm pots | 6 to 7 | 5 to 7 |
| Natural season flower date: | | |
| in Salinas, CA | Aug 20 to 25 | Aug 26 to Sep 11 |
| in Hightstown, NJ | Sep 27 to 29 | Sep 24 to 30 |
| Flow. resp. in spring | 47 to 48 days | 53 to 63 days |
| Plant height: | | |
| in nat. season fall NJ | 36 cm | 30 to 38 cm |
| in nat. season fall CA | 23 to 25 cm | 20 to 28 cm |
| in 10 cm pots spring | 23 to 25 cm | 20 to 23 cm |

COMPARISONS MADE OF PLANTS GROWN AS UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Emily, as described and illustrated.

* * * * *

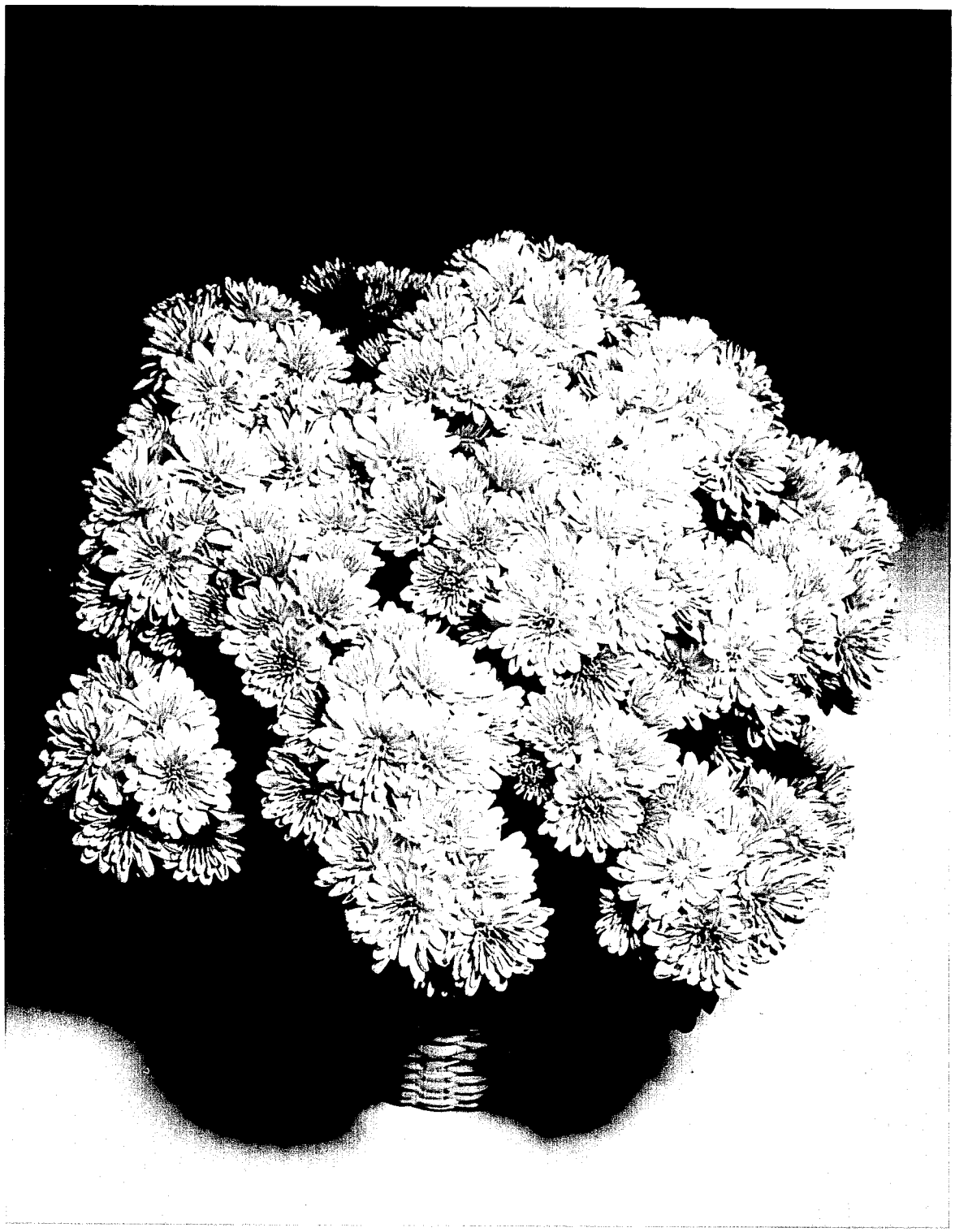

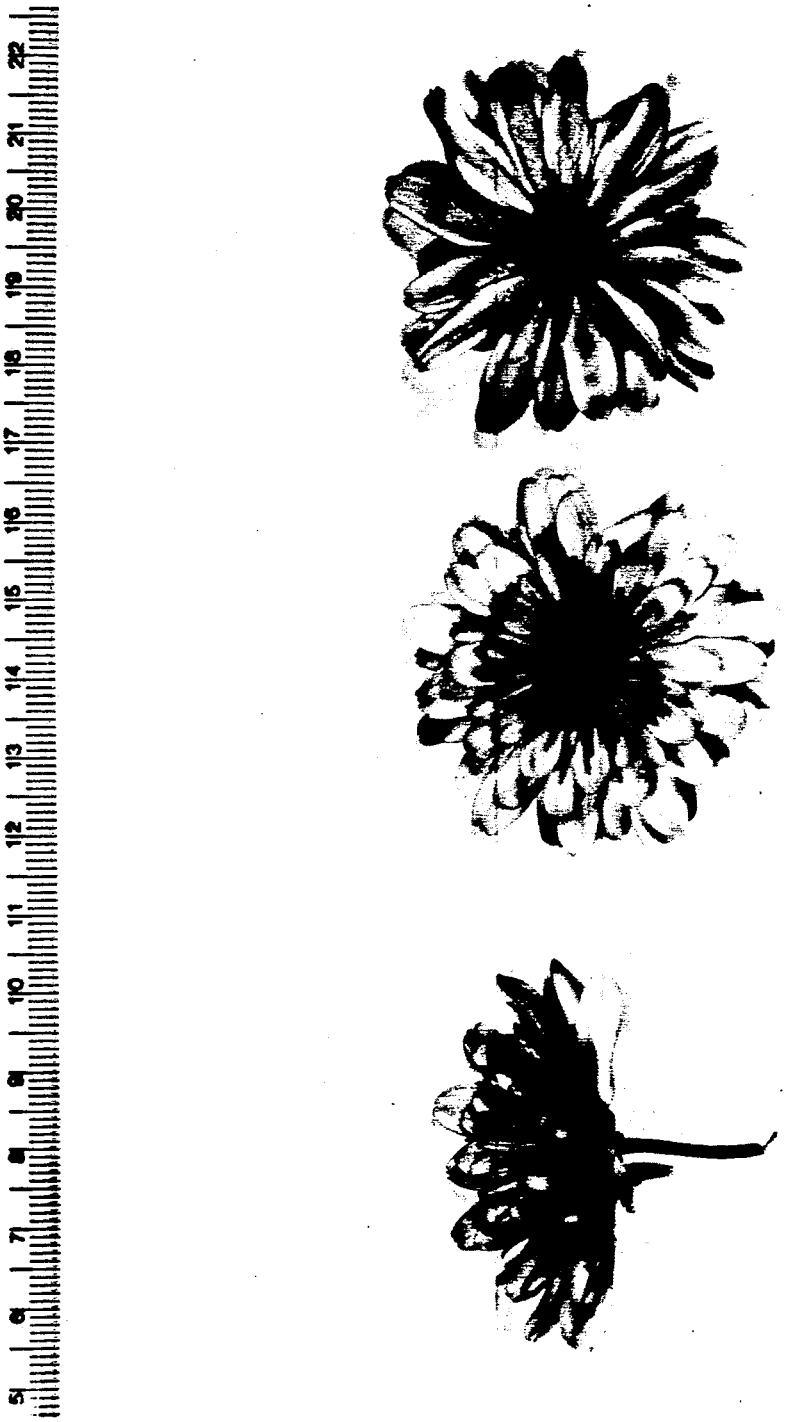
5
6
7
8
9
10
11
12
13
14
15
16
17
18
19
20
21
22

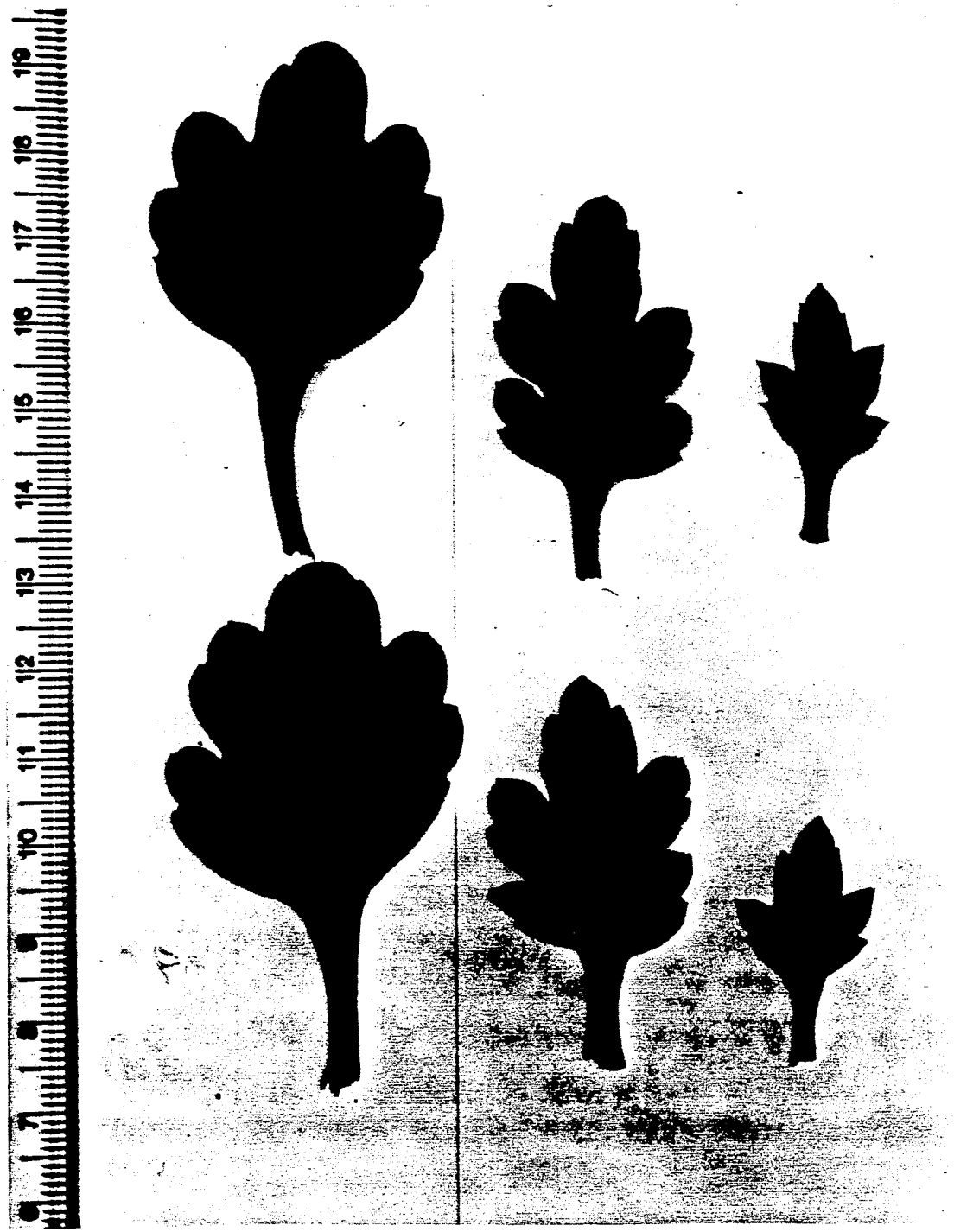
6
7
8
9
10
11
12
13
14
15
16
17
18
19